United States Patent [19]

Nelms

[11] 3,964,490

[45] June 22, 1976

[54] LEAD STORAGE APPARATUS FOR ELECTROMEDICAL DEVICE

[75] Inventor: George E. Nelms, Minneapolis, Minn.

[73] Assignee: Medtronic, Inc., Minneapolis, Minn.

[22] Filed: Jan. 14, 1975

[21] Appl. No.: 540,807

[52] U.S. Cl. .............................. 128/419 R; 128/404; 191/12.4; 339/8 RL
[51] Int. Cl.² ........................................... A61N 1/00
[58] Field of Search ........................... 128/404–418, 128/419 R, 2.06 E, 2.06 R, 2.1 E, 2.1 R, DIG. 4; 339/5 RL, 6 RL, 8 RL, 148; 191/12.2 R, 12.4

[56] References Cited
UNITED STATES PATENTS

| | | | |
|---|---|---|---|
| 780,322 | 1/1905 | Callender | 191/12.2 R |
| 1,958,626 | 5/1934 | Krantz | 191/12.2 R |
| 2,510,624 | 6/1950 | Forshey | 191/12.2 R |
| 2,632,447 | 3/1953 | Dobes | 128/404 |
| 2,710,610 | 6/1955 | Woodruff | 128/406 |
| 2,937,396 | 5/1960 | Momberg et al. | 191/12.2 R |
| 3,178,128 | 4/1965 | Meletti | 191/12.2 R |
| 3,773,987 | 11/1973 | Davis et al. | 191/12.4 |
| 3,821,496 | 6/1974 | Malone | 128/2.06 E |

OTHER PUBLICATIONS

"GE Diathermy Electrode and Accessories" July, 1934, pp. 4–7, 14, 26.

*Primary Examiner*—Robert W. Michell
*Assistant Examiner*—Lee S. Cohen

[57] ABSTRACT

An electromedical device including cable leads for delivering an electrical signal to the desired situs of a patient's body, such device having a storage mechanism for the cable leads which allows a length of the cable leads to be withdrawn and, by use of a locking mechanism associated therewith, allows the cable leads to be held in place while the cable leads are in use and also allows such cable leads to be automatically returned to the storage mechanism upon release of the locking mechanism.

1 Claim, 4 Drawing Figures

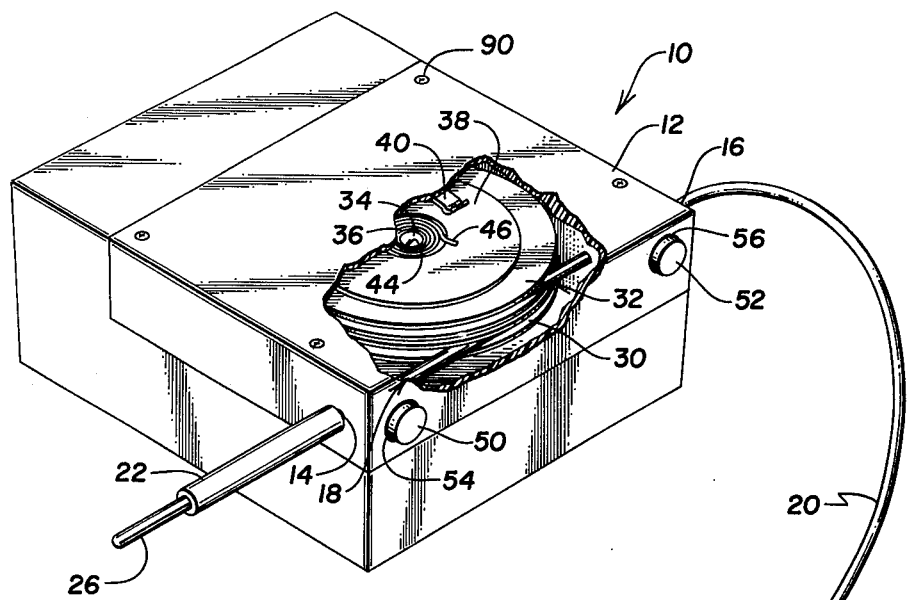
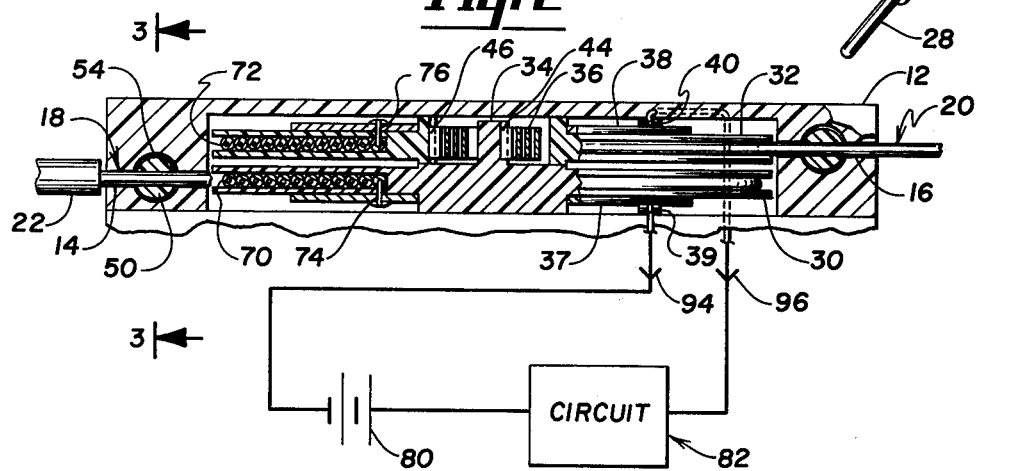
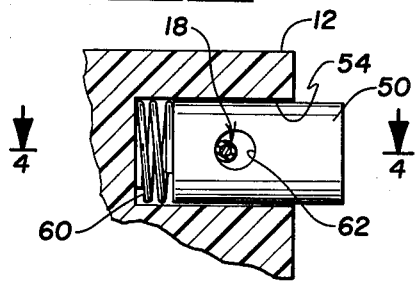
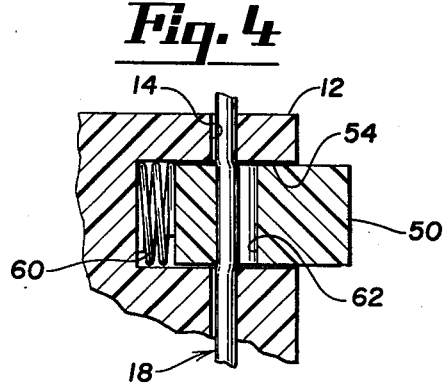

LEAD STORAGE APPARATUS FOR ELECTROMEDICAL DEVICE

This invention relates to an electromedical device and more particularly to a mechanism for releasably storing the electrical cable leads associated with such a device. The invention has special but not exclusive application to external electrical stimulator devices and it is with respect to such a device that the invention will be described.

External stimulator devices such as that commercially available through Medtronic, Inc. under the name Neuromod™ Transcutaneous Nerve Stimulator utilize electrical lead cables which conduct the electrical stimulus to the desired position on the skin of the patient. A problem associated with the usage of such transcutaneous stimulator devices has been the inconvenience associated with maintaining exceptionally long cables out of the ambulatory patient's way. Normally, excessive portions of the cables are coiled adjacent to the stimulator and taped to the patient's skin or otherwise draped inside the patient's clothing. The cables thus receive excessively rough treatment in this process. In addition, the rather lengthy leads are inconvenient to store during nonuse of the stimulator.

The invention herein described, which ameliorates the problem, constitutes an improvement in such electromedical devices having main housing means, power supply means, electronic signal circuitry, and lead means for electrically connecting the electronic signal circuitry to a remote situs, such improvement comprising reel means for storing the lead means, the reel means being adapted to allow manual withdrawal of a length of lead means therefrom, retracting means adapted to exert a retracting force capable of causing said length of said lead means to retract into storage relationship on the reel means, and selectively activatable locking means adapted to exert a locking force on the lead means in excess of the retracting force whereby the length of said lead means can be maintained in a withdrawn position only while said locking means is activated.

The invention will be described in conjunction with the drawings wherein:

FIG. 1 is a pictorial view with a portion cut away to illustrate internal elements of the lead storage reel in association with the housing of an electrical stimulator;

FIG. 2 is a cut-away view in elevation showing elements of the lead storage reel of this invention;

FIG. 3 is a section taken along lines 3—3 of FIG. 2 depicting a locking mechanism; and FIG. 4 is a section taken along lines 4—4 of FIG. 3 depicting the mechanical restraint placed upon the lead by the locking mechanism.

Referring to FIG. 1, a stimulator housing 10 has a box-like appearance and is preferably constructed of a high impact resistant material that fully encases electrical pulse generating circuitry and a power supply therefor (not shown). The electrical stimulating circuitry and power supply may be those employed in the device currently available from Medtronic, Inc. under the trade designation Neuromod™ Transcutaneous Nerve Stimulator. Such a transcutaneous nerve stimulator provides a versatile therapeutic method which employs the passage of small electrical currents through the skin. These currents are known to effect depolarization (propagating stimulation) of sensory nerve endings and of nerves themselves. Such depolarization results from the passage of impulses along effected nerves. These impulses further effect peripheral and central mechanisms, which are as yet not fully clarified, resulting in the effective inhibition (awareness or perception) of certain normal sensations, most notably pain.

Referring back to FIG. 1, the housing 10 depicted therein does not exactly conform to that currently used to house the Neuromod™ Transcutaneous Nerve Stimulator. Also for convenience sake, the external control mechanism, such as an externally adjustable potentiometer, for controlling the rate of electrical stimulation as well as its amplitude, is not depicted in FIG. 1. Furthermore, the housing 10 of FIG. 1 may include on its reverse side a spring clip that would fit over the trouser belt of a patient using the electrical stimulator.

Associated with the stimulator housing 10 depicted in FIG. 1 is a lead storage mechanism housing 12 preferably constructed of the same high impact material as is housing 10. Extensible from two circular openings 14 and 16 on opposite sides of the housing 12 are leads or cables 18 and 20, each of which comprises an electrical conductor of predetermined length coated or insulated by an insulating plastic material. As explained with reference to FIG. 2, the proximal ends of the cables 18 and 20 are attached to the reels within the housing. The terminal ends of cables 18 and 20 comprise insulating electrode heads 22 and 24 of a greater cross section than either the leads 18 and 20 or the circular openings 14 and 16. Heads 22 and 24 thus serve as stops preventing further withdrawal of the lead cables into housing 12. Emerging from the ends of the electrode heads are the metallic conductor pins 26 and 28. The conductor pins 26 and 28 are adapted to be connected to preformed female connector terminals in association with skin electrodes (not shown). The electrodes may take any form suitable for applying electrical stimulus transcutaneously, and such electrodes are well known in the art. The preferred electrodes comprise a plate-like, pliant electrically conductive material that may adhere to the skin either by itself or may be secured in place with tape or other appropriate methods. Such electrodes also have formed integrally with the electrode surface area the mating female electrical receptacle for receiving the terminal pins 26 and 28. In operation, electrical stimuli developed by the pulse stimulator are conducted through one of the cables 18 and 20 and its associated electrode to the skin of the patient and through the patient and the other of the electrodes and its associate cable back to the electrical stimulator, in a manner of application well known in the art.

Referring to the cut-away portion of the housing 12 in FIG. 1, there is shown first and second lead storage reels 30 and 32. The lead storage reels 30 and 32 are circular in shape and share a common axis 34 about which they rotate independently in opposite directions from one another. The lead storage reels 30 and 32 are preferably constructed of an electrically nonconducting high impact strength material. The reels 30 and 32 are mounted one above another and the reels are associated with a common coil spring 36. Also, each reel has on one surface thereof an electrically conductive plate 37 or 38 and an associated brush 39 and 40, respectively, that bears against the generally circular electrically conductive plate to provide continuous electrical contact between the plate and the output circuitry of the pulse generator circuit.

Referring now to FIG. 2, there is shown a cut-away view in elevation of the reels 30 and 32 and their association with the cables 18 and 20, respectively. The reel 32 is coaxially mounted for free rotation about an axial member 34 extending from and forming a part of the hub of reel 30. A spiral tension spring 36 attaches at its ends the axial member 34 and the hub of reel 32, as shown at points 44 and 46, respectively, in FIG. 1.

Due to the fact that the electrode cables 18 and 20 are drawn out of opposite sides of the housing 12 as shown in FIG. 1, it is necessary that the reels 30 and 32 rotate in opposite directions with respect to one another during the time that the cables 18 and 20 are extended. As the cables 18 and 20 are withdrawn from the housing 12, the reels 30 and 32 are rotated in a counter-clockwise direction against the retracting force of the coiled spring 36. Consequently, upon release of the cables 18 and 20, the coiled spring 36 will retract the cables 18 and 20 by rotating the reels 30 and 32 in a clockwise direction. It may be recalled that the metal pins 26 and 28 of the electrode heads 22 and 24 are adapted to engage the female connectors of skin electrodes on the patient's body. It is necessary, therefore, that the patient be able to withdraw a suitable length of the cables 18 and 20 to connect the metal pins 26 and 28 to the electrodes and to retain the leads in contact with the electrodes without an undue amount of stress placed on the cable itself, the electrode connector, or the electrode itself in contact with the patient's skin. If the cables 18 and 20 are simply withdrawn to a suitable length and attached to the electrodes, the tension of the coiled spring 36 acting on the reels 30 and 32 will tend to break the electrical contact of the electrode with the patient's skin or disconnect the metal pins 26 and 28 from the electrode connectors, especially as the patient moves about. To prevent this from happening, by the practice of this invention, there are provided in association with the cables 18 and 20 locking means for locking or retaining a section of the cables 18 and 20 in a stationary relationship with respect to the housing 12 in order to overcome the retracting force exerted by the spiral spring 36.

Referring now to FIGS. 3 and 4 with respect to FIGS. 1 and 2, a preferred form of the locking means is shown. The locking means comprise a pair of buttons 50 and 52 which project from respective bores 54 and 56 in the housing 12. As shown in FIG. 1, the bores 54 and 56 extend from a common surface of the housing 12 perpendicularly with respect to and in communication with the openings 14 and 16. With reference to FIG. 2, the buttons 50 and 52, disposed in the bores 54 and 56, respectively, are depicted in an internal cutaway view in contact with a length of the cables 18 and 20 extending through the bores 14 and 16, respectively. With reference to FIG. 3, there is shown a cut-away view of the button 50 along the section line 3—3 of FIG. 2. A portion of the button 50 extends from the surface of the housing 12 depicted in FIG. 1. The bore 54 in the housing 12 extends for a predetermined depth. A coiled wire spring 60 is disposed within the bore 54 and in contact with the end of the bore 54 and the end of the button 50. The button 50 contains a further bore 62 which extends diametrically through the button 50 at a point with respect to housing 12 that is axially common with the bore 14 in housing 12. Located within the bore 62 is the section of the cable 18 depicted in FIG. 2 as traversing the button 50.

Referring now to FIG. 4, there is shown a sectional view taken along line 4—4 of FIG. 3 of the locking means for retaining the cables in a stationary extended position with respect to the housing 12. The view of FIG. 4 is a top sectional view of the structure depicted in FIG. 3. In the view of FIG. 4 the axial cooperation of the opening 14 in housing 12 with the bore 62 and button 50 is shown. Cable 18 traverses both the opening and the bore. The locking means allowing the patient to withdraw a desired length of cables 18 and 20 against the force of the coiled spring 36 by depressing or deactivating the buttons 50 and 52 so that the openings 14 and 62, for example, are axially aligned. Then the cables 18 and 20 may be freely withdrawn. Once desired lengths of cables 18 and 20 have been withdrawn from the reel storage housing 12, the patient may activate the locking means by releasing the buttons 50 and 52, and the coiled spring 60 will force the buttons 50 and 52 away from and out of the bores 54 and 56. And, as shown with particularity in FIG. 4, the bore 62 will exert a force against a section of the cables traversing the bore thus tending to distort the straight path followed by the cable 18 through the opening 14 and bore 62. The cable 18 will thereby be frictionally engaged by the opening 14 and bore 62 at the point where the cable traverses these passages.

Referring back to FIGS. 1 and 2, it will be noted that the turns of the cables 18 and 20 on the reels 30 and 32, respectively, are depicted at points 70 and 72, respectively. The proximal ends of cables 18 and 20 are electrically attached by feed-through terminals 74 and 76 which mechanically restrain the cables 18 and 20, so that they may not be entirely withdrawn from the housing 12 and also provide electrical contact from the electrical conductor of the cables through the insulating materials of the reels 30 and 32 and to the electrically conductive plates 37 and 38, respectively. The plates 37 and 38 are discshaped and have a diameter sufficient to allow the electrical brush contacts 39 and 40 to ride along and contact the electrically conductive surfaces of the plates 37 and 38 through 360° of rotation of the reels 30 and 32. It will be understood that the position of the plates 37 and 38 and the brush contacts 39 and 40 may be reversed, so that the plates are stationary on the inner walls of housing 12 and the brushes rotate with the reels.

Referring again to FIG. 2 there is also depicted in block form the electrical connection of the pulse generator circuit of the stimulator to the plates 37 and 38, so that the electrical stimuli developed by the circuit may be applied to the electrodes at the proximal ends of the cables. More particularly, a battery 80 is shown electrically connected with a pulse generator circuit 82 which in turn is electrically connected through brush 40 and plate 38, to the electrically conductive cable 18 by means of feed-through terminal 76. Electrically conductive cable 18 is connected to a skin electrode (not shown) attached to the patient's skin, and a similar skin electrode (not shown) attached to the patient's skin is intended to be connected to cable 20 in the same manner. The electrical circuit is completed from cable 18 through feed-through terminal 74, plate 37 and brush 39 back to the battery 80. In this manner, stimulating impulses produced by the circuit 82 are applied via electrodes attached to the patient's skin in a manner well known in the art, and a return electrical circuit is effected from the patient to the pulse generator.

Another aspect of my invention concerns the ease with which the reel housing 12 may be removed from the housing 10 for service or replacement. More particularly, as described hereinbefore, both housings 10 and 12 are self-contained, and housing 12 is fastened to housing 10 by means of four fasteners 90, e.g., screws in threaded holes extending from housing 12 into housing 10 as shown in FIG. 1. In addition, there are provided convenient electrical connectors 94 and 96 for electrically disconnecting the battery 80 and circuit 82 from the brushes 39 and 40 when the reel housing 12 is removed from the stimulator housing 10. These connectors may take any of the many forms known in the prior art but are preferably miniature units of the pin and socket type.

What is claimed is:

1. In an electromedical device having main housing means housing power supply means and electronic signal circuitry electrically connected to said power supply means; reel means; and elongated lead means associated with said reel means for electrically connecting said electronic signal circuitry to a remote situs; the improvement which comprises: reel housing means detachably connected to said main housing means, said reel housing means housing said reel means, said reel means comprising at least two reels mounted on a common axis, an equivalent number of said lead means each associated with a single reel, said reels being electrically insulating and independently rotatable in opposing directions to allow withdrawal of a length of its respective lead means therefrom, retracting means adapted to exert a retracting force capable of causing said length of said lead means to retract into storage relationship on its respective reel, said reel housing means having port means providing a passage for each of said lead means from said reel means to the exterior of said reel housing means, and selectively activatable locking means communicating with said port means to prevent movement of each of said lead means through said port means, the number of port means and locking means being equivalent to the number of said reels and said lead means, and an equivalent number of aperture means in said reel housing means for slidably receiving each of said locking means, each of said locking means comprising plunger means having a channel extending through said plunger means dimensioned to allow passage therethrough of said lead means, each of said channels communicating with its respective port means, and spring means located in each of said aperture means positioned to enable operation of said plunger means, said spring means in its relaxed state maintaining said channel of said plunger means such that said locking means is in a locking position preventing movement of said lead means through said port means, and said spring means in its loaded state maintaining said channel of said plunger means such that said locking means is in a nonlocking position wherein movement of said lead means through said port means is permitted.

* * * * *